United States Patent [19]

Nakagawa et al.

[11] Patent Number: 4,882,359

[45] Date of Patent: Nov. 21, 1989

[54] AZACYCLOALKANE DERIVATIVES, ABSORPTION PROMOTERS CONTAINING THE DERIVATIVES AS THE EFFECTIVE INGREDIENT AND EXTERNAL PREPARATIONS CONTAINING THE ABSORPTION PROMOTERS

[75] Inventors: Akira Nakagawa, Tosu; Michinori Sakai, Mizuma, both of Japan

[73] Assignee: Hisamitsu Pharmaceutical Co., Ltd., Tosu, Japan

[21] Appl. No.: 131,193

[22] Filed: Nov. 18, 1987

[30] Foreign Application Priority Data

Apr. 8, 1986 [JP] Japan .................................. 61-79174
Feb. 10, 1987 [WO] PCT Int'l Appl. ....PCT/JP87/00086

[51] Int. Cl.[4] .................... A61K 31/40; A61K 31/395; A61K 47/00
[52] U.S. Cl. .................................... 514/947; 514/946; 514/424; 514/183; 548/551; 540/451
[58] Field of Search .................. 548/551; 540/451; 514/947, 424, 183

[56] References Cited

U.S. PATENT DOCUMENTS

| | | | |
|---|---|---|---|
| 3,188,317 | 6/1965 | Hickner | 548/551 |
| 3,228,955 | 1/1966 | Hickner | 548/551 |
| 3,232,952 | 1/1966 | Seeliger | 260/358 X |
| 3,956,313 | 5/1976 | Freyermuth | 548/551 |
| 3,991,203 | 11/1976 | Rajadhyaksha | 514/946 |
| 4,415,563 | 11/1983 | Rajadhyaksha | 514/947 |
| 4,423,040 | 12/1983 | Rajadhyaksha | 514/947 |
| 4,424,210 | 1/1984 | Rajadhyaksha | 514/947 |
| 4,444,762 | 4/1984 | Rajadhyaksha | 514/947 |

FOREIGN PATENT DOCUMENTS

| | | |
|---|---|---|
| 871154 | 3/1953 | Fed. Rep. of Germany . |
| 1695846 | 5/1971 | Fed. Rep. of Germany . |
| 2114251 | 10/1971 | Fed. Rep. of Germany . |
| 2114295 | 10/1971 | Fed. Rep. of Germany . |
| 2117240 | 10/1971 | Fed. Rep. of Germany . |
| 947910 | 1/1964 | United Kingdom . |
| 2118438 | 11/1982 | United Kingdom . |
| 2118553 | 11/1983 | United Kingdom . |

*Primary Examiner*—David B. Springer
*Attorney, Agent, or Firm*—Bucknam and Archer

[57] ABSTRACT

An azacycloalkane derivative useful for promoting the absorption of a medicine, an absorption promoting agent comprising at least one of the azacycloalkane derivatives as the effective ingredient for promoting the absorption and an external preparation containing the absorption promoting agent, the derivative being represented by the following formula

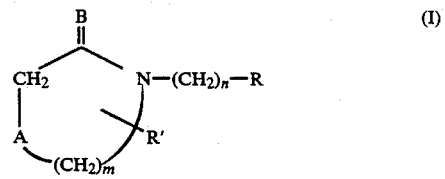

wherein A is —$CH_2$— or —S— for example, B is sulfur or oxygen, R is —SR″ in which R″ is an alkyl group or alkylthioalkyl group for example, or —OR″ in which R″ is as defined above, an alkyl group or substituted amino group, R′ is a hydrogen atom, alkyl group or alkyloxy group for example, m is an integer of 0–5 and n is an integer of 1–15.

10 Claims, No Drawings

AZACYCLOALKANE DERIVATIVES, ABSORPTION PROMOTERS CONTAINING THE DERIVATIVES AS THE EFFECTIVE INGREDIENT AND EXTERNAL PREPARATIONS CONTAINING THE ABSORPTION PROMOTERS

BACKGROUND OF THE INVENTION

1. Field of the Invention

This invention relates to azacycloalkane derivatives which increase the permeability and penetrability of other medicines and have low irritating actions on live body membranes and low systemic toxicities and also to absorption promoters containing said derivatives as the effective ingredient. The compounds, azacycloalkanes, of this invention are useful not only in drugs but also cosmetics, agricultural chemicals, insecticides and the like which are other than medicines, and as agents for promoting the permeation of medicines.

2. Prior Art

Absorption promoters which have now been known, include organic solvents such as dimethylsulfoxide, dimethylacetamide and pyrrolidone, 1-n-dodecylazacycloheptane-2-one (Azone) and the like described in Japanese Pat. Appln. Laid-Open Gazette No. 52-1035, and N-(2-hydroxyethyl) pyrrolidone and the like described in Japanese Patent Applns. Laid-Open Gazettes Nos. 60-13711 and 60-36423.

In addition, "Z hur. obshchei Khim. 30, 4108 (1960)" reports 1-(2-propylthioethyl) azacyclopentane2-one but however, it neither discloses nor suggests anything about the absorption promoting action exhibited by the compounds of this invention.

[Problems Intended To Be Solved By This Invention]

There has recently been increasingly an interest in the development of pharmaceuticals useful for promoting percutaneous absorption. The reason for this is that when there are administered medicines which are expected to have percutaneously topical or systemic pharmacological actions, the efficacy of the medicines can be endured, the absorption rate thereof can be easily adjusted, the prevention of side effects caused by over-administration of the medicines is possible, effects and the like of metabolism due to first-time passage through the liver as in the case of oral administration and the like are slight thereby to enable the effective use of the medicines, and the medicines may be administered with comparative safety even if they are those which will cause liver troubles and the like when used. Because normal body skins naturally have protective actions on irritations from the outside, it is deemed comparatively difficult that medicines are absorbed and permeated through the skins. Even if, medicines are administered in the form of an ointment, cream, gel, lotion of plaster, it is difficult at present to permit medicines to be easily absorbed in such a necessary amount as to achieve the desired medicinal efficacy fully.

There are several drugs which are permeable or penetrable with difficulty through a live body membranes even if they are administered percutaneously, orally, rectally, palatally, nasally or sublingually. Thus, they have low bioavailability.

There have accordingly been sought absorption-promoting agents which fully increase the permeability, penetrability and absorbability of drugs through live body membranes such as the skin, which exhibit satisfactory pharmacological effects when used in a practical concentration, have themselves low topical and systemic toxicities and are highly useful and safe.

The presently known absorption promoters are still not satisfactory enough to enhance the bioavailability of medicines which are poorly permeable and penetrable through live body membranes, and, further, some of them are irritating to the skin and cause the textures to discolor with remarkable side effects when repeatedly administered. Therefore, they are limited in general application and manner of use, this leaving the problem of their practicality unsolved.

The present inventors made intensive studies in attempts to develop compounds which are highly safe and have excellent absorption-promoting actions in a practical concentration greater than those of the heretofore known dimethylsulfoxide and azacycloalkane derivatives and, as the result of their studies, they found that the desired compounds are azacycloalkane derivatives wherein one or two ether bonds, thioether bonds or amino bonds are substituted at the N-position, or azacycloalkane derivatives wherein one methylene chain is substituted by an oxygen atom or a sulfur atom. These desired compounds are fully suitable for the purpose of this invention and are the very compounds of this invention.

SUMMARY OF THE INVENTION

This invention relates to specific azacycloalkane derivatives and also to absorption-promoting agents containing as the effective ingredient at least one compound selected from said specific azacycloalkane derivatives represented by the following formula (I):

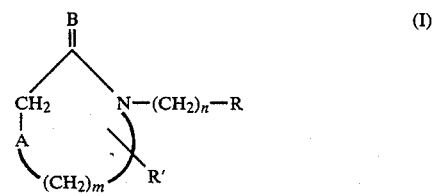

wherein A is —$CH_2$—, —S— or —O—, B is sulfur or oxygen, R is —SH" or —OR" (in which R" is an alkyl group, alkylthioalkyl group, alkyloxyalkyl group, substituted aminoalkyl group, phenyl group, substituted phenyl group, benzoyl group, substituted benzoyl group or heterocyclic group), an alkyl group or substituted amino group, R' is a hydrogen atom, alkyl group, alkyloxy group, acyloxy group, alkylthio group, hydroxyl group, carboxylic group or alkyloxycarbonyl group having 1–12 carbon atoms, m is an integer of 0–5 and n is an integer of 1–15 with the proviso that R does not contain an alkyl group.

The symbols R, R' and R" in the general formula (I) are explained hereinafter in more detail. The alkyl group represented by the symbol R is a straight-chain or branched-chain alkyl group having 1 to 20 carbon atoms such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or eicosyl group.

The substituted amino group represented by the symbol R is (1) —NH—$R^1$ wherein $R^1$ means an alkyl group of 1 to 20 carbon atoms, (2)

wherein $R^1$ and $R^2$ each mean an alkyl group of 1 to 20 carbon atoms, (3) a cyclic amino group such as pyrrolidino, piperidino, morpholino, piperadino or

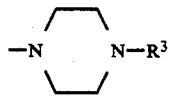

wherein $R^3$ means a low alkyl group, low alkyl group substituted by hydroxyl group, benzyl group or a substituted benzyl group (e.g. the substituent includes a low alkyl group, low alcoxy group, hydroxyl group, a halogen atom, trifluoromethyl group, nitro group, amino group, carboxyl group or an ester thereof) or (4) —N-H—$R^4$ wherein $R^4$ includes phenyl group, benzoyl group, a substituted phenyl group, a substituted benzoyl group (e.g. the substituent includes a low alkyl group, low alcoxy group, hydroxyl group, a halogen atom, trifluoromethyl group, nitro group, amino group, carboxyl group or an ester thereof) or a heterocyclic group (e.g. pyridyl, thiophene, furan, thiazol, isothiazol, isooxazol, pyrimidine, pyrazol, pyrazine, pyran, pyrrol or pyridazine group).

The alkyl group represented by the symbol R' is an alkyl group having 1 to 20 carbon atoms, an alkyloxy group including methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy or eicosyloxy group, an alkylthio group including methylthio, ethylthio, propylthio, butylthio, pentylthio, hexylthio, heptylthio, octylthio, nonylthio, decylthio, undecylthio, dodecylthio, tridecylthio, tetradecylthio, pentadecylthio, hexadecylthio, heptadecylthio, octadecylthio, nonadecylthio or eicosylthio group, or an alkyloxycarbonyl group having 1 to 12 carbon atoms including methoxycarbonyl, ethoxycarbonyl, propoxycarbonyl, butoxycarbonyl, pentyloxycarbonyl, hexyloxycarbonyl, heptyloxycarbonyl, octyloxycarbonyl, nonyloxycarbonyl, decyloxycarbonyl, undecyloxycarbonyl or dodecyloxycarbonyl group. Further, R' includes acyloxy, hydroxyl or carboxyl group.

The alkyl group represented by the symbol R" is an alkyl group having 1 to 20 carbon atoms, an alkyl substituent in the alkylthioalkyl, alkyloxyalkyl or substituted aminoalkyl group means an alkyl group having 1 to 20 carbon atoms as mentioned above. An amino substituent in the substituted aminoalkyl group means the substituted amino group in the R as mentioned above. Further, the substituted phenyl or substituted benzoyl group includes phenyl or benzoyl group having 1 to 3 substituents in any part wherein the substituent includes a halogen atom such as fluorine, chlorine, bromine or iodine atom; a low alcoxy group such as methoxy, ethoxy, propoxy or butoxy group; a low alkyl group such as methyl, ethyl, propyl, butyl, pentyl or hexyl group; hydroxy group; trifluoromethyl group; an acyloxy group; nitro group; an amino group; a carboxyl group; an alkyloxycarbonyl group having 1 to 12 carbon atoms as mentioned above. The heterocyclic group includes pyridyl, thiophene, furan, thiazol, isothiazol, isooxazol, pyrazol, pyrazine, pyran, pyrrole or pyridazine.

The compounds of this invention may be prepared in a good yield by the following methods or even by other known methods.

Methods for preparing the compounds of this invention are illustrated as follows.

Preparation 1

The sequence of chemical reactions for preparing the compounds of this invention is indicated below:

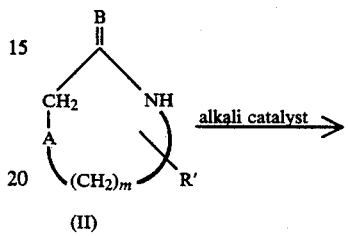

(II)

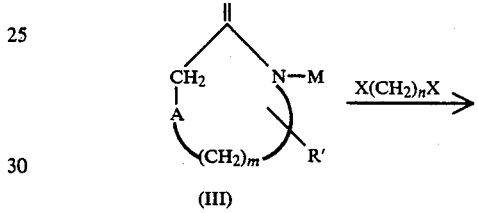

(III)

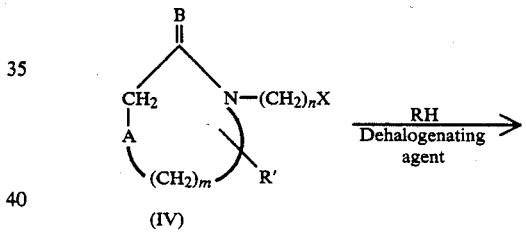

(IV)

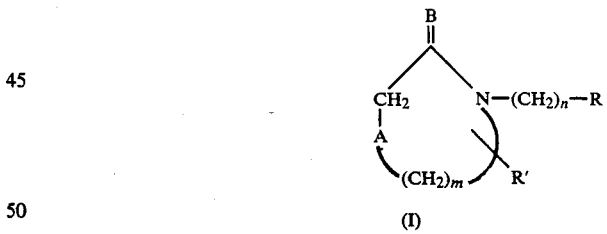

(I)

wherein M is alkali metal ion, X is a halogen atom, mesyl group or tosyl group, R is —SR" (in which R" is as previously defined) or substituted amino group, and R', A, B, m and n are respectively as previously defined.

More particularly, a compound (II) is treated at a temperature of 0°–300° C., preferably 0°–100° C. for about 0.5-20 hours, within or without a nitrogen gas atmosphere in a solvent which does not participate the reaction (such as benzene, toluene, tetrahydrofuran, methanol, ethanol, dimethylformamide or dimethylsulfoxide) and in the presence of either an alkali catalyst such as a sodium alcoholate or sodium hydride, or an interlayer transfer catalyst such as tetra-n-butylammonium hydrogen sulfate, thereby to produce a compound (III). The compound (III) is incorporated with a dihalogenoalkane in an excessive molar ratio to synthesize a compound (IV). The thus synthesized compound (IV) is then treated with a thiol or amine at a temperature of 0°–300° C., preferably 0°–100° C., for about 0.5 hours to about 3 days within or without a nitrogen gas atmosphere, in an inert solvent (such as benzene, toluene, tetrahydrofuran, methanol, ethanol, dimethylformamide or dimethylsulfoxide) which does not participate the reaction and in the presence of a known dehalogenating agent (such as 1,5-diazabicyclo-[4,3,0]nonene-5 (DBN) or 1,8-diazabicyclo[5,4,0] undecene-7(DBU)), thereby to obtain an end compound (I).

Preparation 2

As indicated by the following reaction

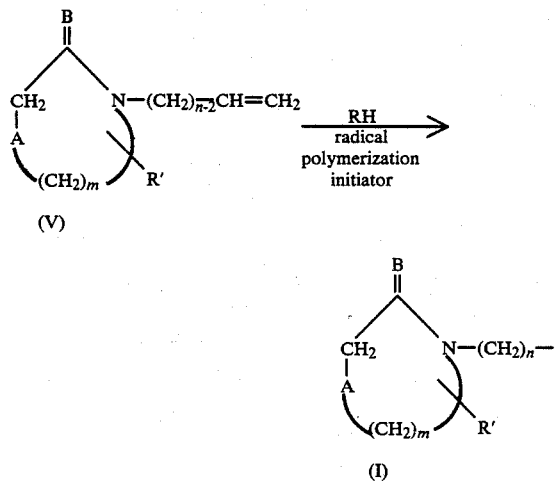

wherein R is —SR" (R" is as previously defined: n means an integer of from 2 to 15), and R'. A,B and m are respectively as previously defined, the compound (V) is treated with a thiol at a temperature of 0°–150° C. for 2–18 hours within or without a nitrogen gas atmosphere in an inert solvent (such as benzene, toluene or xylene) which does not participate the reaction and in the presence of a known radical polymerization initiator (such as benzoyl peroxide or azobisisobutyronitrile), thereby to obtain the end compound (I).

Preparation 3

As is shown in the following reaction

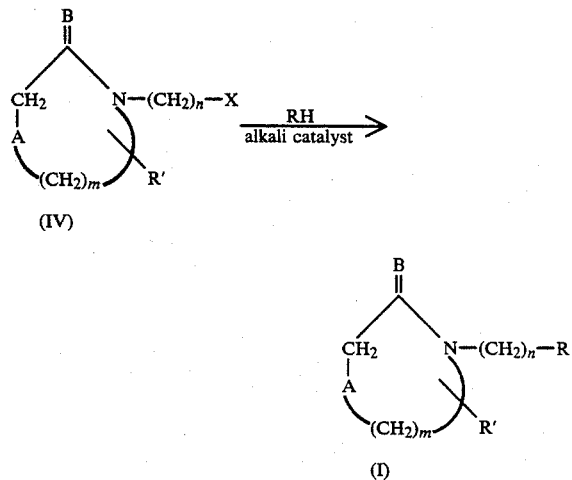

wherein X is a halogen atom, mesyl group or tosyl group, R is —OR" (R" are as previously defined), and R', A, B, m and n are respectively as previously defined, the intermediate compound (IV) as synthesized by means of Preparation 1 is treated with an alcohol at a temperature of 0°–300° C., preferably 0°–100° C. for about 2–about 10 hours in an alcoholic solvent or a solvent (such as benzene, toluene, dimethylformamide or dimethylsulfoxide) which does not participate the reaction and in the presence of an alkali catalyst (such as a sodium alcoholate, sodium hydride or potassium hydride), thereby to obtain the end compound (I).

Preparation 4

As indicated in the following sequence of chemical reactions

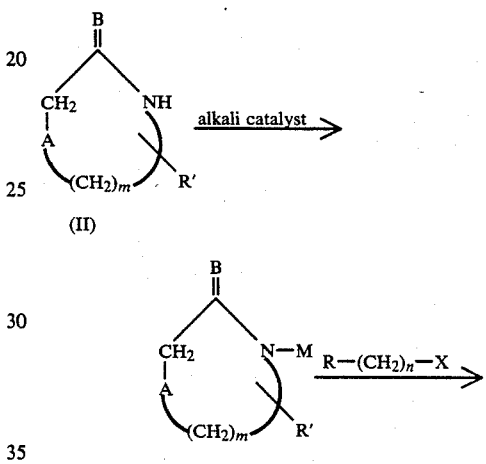

wherein M is alkali metal ion, X is a halogen atom, mesyl group or tosyl group, R is an alkyl group, A is —S— or —O—, and R', B, m and n are respectively as previously defined, the cyclic compound (II) is treated at a temperature of 0°–300° C., preferably 0°–100° C. for about 0.5–about 20 hours within or without a nitrogen gas atmosphere in a solvent (such as benzene, toluene, tetrahydrofuren, methanol, ethanol, dimethylformamide or dimethylsulfoxide) which does not participate the reaction and in the presence of an alkali catalyst such as either a sodium alcoholate or sodium hydride, or an interlayer transfer catalyst such as tetra-n-butylammonium hydrogen sulfate, thereby to produce the compound (III) which is then treated with an alkyl halide to obtain the end compound (I).

Preparation 5

As indicated in the following sequence of reactions

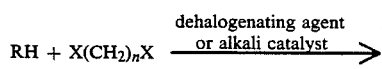

-continued

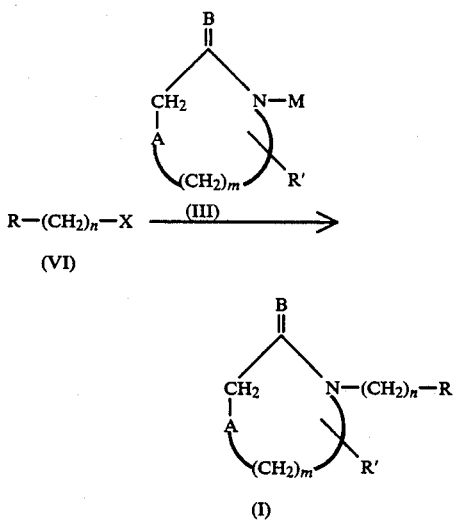

wherein M is alkali metal ion, X is a halogen atom, mesyl group or tosyl group, R is —SR", —OR" (R" is as previously defined) or a substituted amino group, and R', A, B, m and n are respectively as previously defined, the end compound (I) may be obtained in a good yield in accordance with a conventional method for alkylating at the N position.

Preparation 6

As indicated in the following chemical reaction

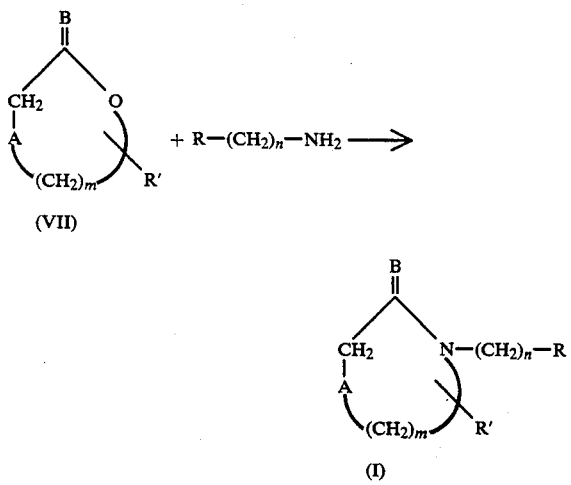

wherein R, R', A, B, m and n are respectively as previously defined, the compound (VII) is treated with an alkylamine to obtain the end compound (I).

The drugs used together with the compounds of this invention are those which have such low permeability or penetrability through live body membranes as to need a promoting agent. They include antibiotics, chemotherapeutic agents, bacteriostatic agents, antimicrobials, disinfectants, antifungal agents, non-steroidal anti-inflammatory agents, steroidal anti-inflammatory agents, carcinostatic agents, psychotropic drugs, local anestetics, antiperkinsonian drugs, sex hormone drugs, anti-sudorific agents, sunscreens, antiallergic agents, antiarrhythmic agents, hypotensive agents, vasodilators, capillary stabilizers, skeletal muscle relaxants, antie-metics, antipsoriatic drugs, skin softeners, emollients, prostaglandins, liposoluble vitamines, enzymes, peptide hormones, antidiabetic drugs, insect repellents, insecticides and agricultural chemicals.

Examples of these medicines which may be used in this invention are as follows.

1. Antibiotic

This pharmaceutical agent includes penicillin type antibiotics such as penicillin G, penicillin V, methicillin, oxacillin, cloxacillin, ampicillin, hetacillin, ciclacillin, amoxicillin, carbenicillin and sulbenicillin; cefalospollin type antibiotics such as cefaloridine, cefalotin, cefazolin, cefaloglycin and cefalexin; aminoglycocid type antibiotics such as streptmycin, kanamycin, dibekacin, gentamicin and fradiomycin; tetracycline type antibiotics such as oxytetracycline, tetracycline and dimethylchlortetracycline, doxycycline and minocycline; macrolide type antibiotics such as erythromycin, leucomycin and josamycin; lincomycin type antibiotics such as lincomycin, clindamycin and lincomycin; and the others such as chloram phenicol, mikamycin, gramicidin, gramicidin S, capreomycin, cycloserine, enviomycin, rifampicin, nystatin, trichomycin, amphotericin B, griseofulvin, variotin, pyrrolnitrin, siccanin, nitrofurantoin, 5-iode-2-deoxyuridine, cefamezin, fosfomycin or N-formimidoylthienamycin-1-hydrate.

2. Chemotherapeutic agent

This pharmaceutical agent includes sulfamides for external use such as mafenide acetate, sulfadiazine, sulfadiazine silver, sulfamethoxazole sodium, sulfisomidine, sulfisomidine sodium or nalidixic acid.

3. Bacteriostatic, disinfectant or antimicrobial

This pharmaceutical agent includes iodine, povidone iodine, diiodohydroxy propane, benzalkonium chloride, benzethonium chloride, methylrosanilinium chloride, hexachlorophene, chlorohexaidine or benzoylperoxide tolnaftate.

4. Antifungal agent

This pharmaceutical agent includes naphthiomate, clotrimazole, griseofulvin, siccanin, trichomycin, nystatin, pyrrolnitrin, exalamide, coloconazole hydrochloride, isoconazole nitrate, econazole nitrate, oxiconazole nitrate, sulconazole nitrate, miconazol, tioconazol, tolciclate, variotin, haloprogin, phenyl 11-iodo-10-undecynoate, bifonazole, naftifin, ketoconazole or cyclopirox olamin.

5. Non-steroidal anti-inflammatory agent

This pharmaceutical agent includes salicylic acid, aspirin, acetaminophen, amino pyrine, antipyrine, oxyphen butazon, sulpyrine, indomethacin, diclofenac sodium, ibuprofen, sulindac, naproxen, ketoprofen, etofenamate, salicylamide, triethanolaminesalicylate, flufenamic acid, meclofenamic acid, colchicine, bufexamac, allopurinol, oxipurinol, ibufenac, fenbufen, diflunisal, alclofenac, phenylbutazone, mefenamic acid, fenoprofen, bendazac, piroxicam or flurbiprofen.

6. Steroidal anti-inflammatory agent

This pharmaceutical agent includes amcinonide, prednisolone acetate valerate, diflucortolone valerate, betamethasone valerate, betamethasone acetate, dexamethasone acetate, betamethasone dipropionate, dexamethasone, triamcinolone acetonide, hydrocortisone, flumethasone pivalate, fluocinonide, fluocinolone acetonide, fluorometholone, fludroxycortide, prednisolone, clobetasol propionate, beclomethasone propionate, betiamethasone, methyl prednisolone, methylprednisolone acetate or hydrocortisone butyrate.

7. Carcinostatic agent

This pharmaceutical agent includes 5-fluorouracil, 6 l-mercaptopurin, methotrexate, bleomycin, mitomycin C, adriamycin, carboquone, actinomycin C, daunorobicin, neocarzinostatin, chromomycin A, L-asparaqinase, picibanil, vinblastine and vincristine.

8. Psychotropic drug

This pharmaceutical agent includes chlorpromazine, chlordiazepoxide, reserpine, etizolam, oxazolam, mexazolam or haloxazolam.

9. Local anesthetic

This pharmaceutical agent includes benzocaine, procaine, propoxycaine, dibucaine, lidocaine, mepivacaine, bupivacaine or tetracaine.

10. Antiperkinsonian drug

This pharmaceutical agent includes L-dopa or chlorzoxazone.

11. Sex hormone drug

This pharmaceutical agent includes estrogen, androgen, estradiol, testosterone or progesterone.

12. Anti-sudorific drug

This pharmaceutical agent includes propantheline bromide, scopolamine or acyloxymethylammonium salt.

13. Sunscreen

This pharmaceutical agent includes p-aminobenzoic acid or p-dimethylamino benzoic acid.

14. Antiallergic agent

This pharmaceutical agent includes sodium cromoglicate or ketotifen.

15. Antiarrhythmic agent

This pharmaceutical agent includes acebutolol, alprenolol, indenolol, carteolol, bucumolol, bufetolol, bupranolol, propranolol or pindolol.

16. Hypotensive agent

This pharmaceutical agent includes reserpine, rescinnamine, rauwolfia alkaloid, clonidine, prazosin, dihydroergotoxine mesylate, meticrane, methldopa, guanethidine or betanidine.

17. Vasodilator

This pharmaceutical agent includes efloxate, etafenone, oxyfedrine, carbocromen, dilazep, diltiazem, trimetazidine, pentaerythrityl tetranitrate, dipyridamole, isosorbide dinitrate, trapidil, nitroglycerine, nifedipine, prenylamine, molsidomine, trolnitrate, inositol hexanicotinate, isoxsuprine, nylidrin nicametate, cyclandelate, cinnarizine, nicotinyl alcohol or heproni-cate.

18. Capillary stabilizer

This pharmaceutical agent includes rutin.

19. Skeletal muscle relaxant

This pharmaceutical agent includes diazepam.

20. Antiemetic

This pharmaceutical agent includes chlorpromazine.

21. Anti-psoriatic drug

This pharmaceutical agent includes methoxsalen.

22. Skin softener or emollient

This pharmaceutical agent includes hydroquinone, urea, heparin or chondroitin sulfate.

23. Prostaglandin

This pharmaceutical agent includes prostaglandin $F_2$, prostacyclin, prostaglandin $E_1$, prostaglandin $E_2$, 7-thiaprostaglandin $E_1$, 16,17,18,19,20-pentanol-15-cyclohexyl-7-thiaprostaglandin $E_1$, 16,17,18,19,20-pentanol-15-cyclopentyl-7-thiaprostaglandin $E_1$, 16,16-dimethyl-7-thiaprostaglandin $E_1$, 17,20-dimethyl-7-thiaprostaglandin $E_1$, 16,17,18,19,20-pentanol-15-cyclohexyl-$\Delta^2$-7-thiaprostaglandin $E_1$, 16,16-dimethyl-$\Delta^2$-prostaglandin $E_1$, 7-fluoroprostacyclin, 5-fluoroprostacyclin, 16,17,18,19,20-pentanol-15-cycrohexylprostacyclin or 16,17,18,19,20-pentanol-15-cycropentylprostacyclin.

24. Fat soluble vitamins and water soluble vitamins

The water soluble vitamins include vitamin $B_1$, vitamin $B_2$, vitamin $B_6$, nicotinic acid, nicotin amide, pantothenic acid, biotin, vitamin $B_{12}$, vitamin C, lipoic acid and inositol.

The fat soluble vitamins include vitamin A, vitamin D, vitamin $D_2$, vitamin $D_3$, vitamin E, vitamin $K_1$, vitamin $K_2$, ubiquinone, vitamin F, 1$\alpha$, 25dihydroxy cholecalciferol, 1,25-dihydroxy vitamin $D_3$, 1$\alpha$-hydroxy vitamin $D_3$, 1,24-dihydroxy vitamin $D_3$, 24,25-dihydroxy vitamin, 1$\alpha$,25-dihydroxy vitamin $D_3$-26,23-lactone and 25-hydroxy vitamin $D_3$-26,23-lactone.

25. Enzyme preparation

This pharmaceutical agent includes trypsin, papain, protease, lysozyme, streptokinase, plasmin, urokinase, hyaluronidase, $\alpha$-chymotrypsin, serratiopeptidase, bromelain or semialkalipeptidase.

26. Peptide hormone

This pharmaceutical agent includes insulin, angiotensin, vasopressin, felypressin, protirelin, gonadotropin hormone, corticotropin, prolactin, somatoropin, thyrotropin, luteinizing hormone, calcitonin, kallikrein, glucagon, oxytocin, gastrin or secretin.

27. Anti-diabetic drug

This pharmaceutical agent includes glibenclamide or gliclazide.

28. Others

Cardiotonic drugs, cough medicines, expectorants, interferon, interloikin and the like.

The compounds of this invention for use as an absorption promoting agent, may be added to the aforementioned medicines in any desired amounts, but they may preferably be added a safe and effective amount of 0.001 to 25%, more preferably 0.01 to 20% of the entire composition.

The absorption promoting agent of this invention and the medicine may be mixed and formed into suppository, plaster, tape, cataplasma, paste, ointment, gel, cream, lotion, liniment, dry syrup, aerosol, tablet, granular or filmy form for use as an external medicine for application to skins, hair or nails or for use as a preparation for application to other live body membranes or the like, the preparation including an orally administered drug, suppository, palatally administered drug, vaginally administered drug, nasally administered drug or eye lotion. Prior to being formed, said mixture or composition may be incorporated with other ingredients depending on the form of a drug to be obtained.

For instance, in a case where the composition is formed into an ointment, it may previously be incorporated with bee wax, a vegetable oil, lanolin, boric acid, white vaseline (Vaseline) and/or the like. When the composition is to be used as a cream agent, it may be incorporated with an oil and fat, wax, higher fatty acid, higher alcohol and/or the like. In the preparation of a lotion from the composition, the composition may be incorporated with ethanol, glycerine, butylene glycol and/or the like. To prepare a solution drug, the composition may usually be incorporated with ethanol, purified water, glycol and/or the like. To make a suspension drug, the composition may be incorporated with traganth, acacia gum, sodium alginate, gelatin, methylcellulose, CMC and/or the like. To prepare a suppository, the composition may be incorporated with cacao butter, palm oil, coconut oil, Vaseline and/or the like. To prepare a tabular drug, granular drug or the like, the composition may be incorporated with methylcellulose, hydroxypropylcellulose, hydroxypropylmethylcellulose, crystalline cellulose, startch and/or the like which are usually used as abase. To prepare a filmy drug, the composition may also be hydroxypropylcellulose, methylcellulose, polyvinylpryrrolidone, polyvinyl alcohol and/or the like.

The thus incorporated compositions containing a pharmaceutical base, the absorption promoting agent of this invention and the medicine may be produced by a conventionally used known method.

PREFERRED EMBODIMENTS

This invention will be better understood by the following non-limitative Examples.

EXAMPLE 1

1.11 g. of N-vinyl-2-pyrrolidone, 1.60 g of n-nonylmercaptane, 8.0 mg of azobisisobutyronitrile and 20 ml of benzene were mixed together and agitated under heat at the refluxing temperature for 2–3 hours. The resulting reaction mixture (liquid state) was washed with water, dried, freed from the solvent by distillation off at reduced pressure and then finally distilled to obtain 2.01 g of colorless 1-[2-(n-nonylthio) ethyl] azacyclopentane-2-one.

The final distillation was effected using a rotary glass-tube oven GTO-250R produced by Shibata Kagaku Kikai K.K. (Shibata Chemical Apparatus Co., Ltd.), Japan. The temperature and pressure at which such distillation was effected are hereinafter expressed in "column temperature" for convenience' sake.

The colorless compound so obtained had the following appearance, column temperature and analysis:

Appearance: Colorless transparent oil.
Column temp.: 122°–127° C./0.2 mmHg.
Analysis: $C_{15}H_{29}NOS$ Theoretical: C 66.37, H 10.77, N 5.16. Found: C 66.43, H 10.62, N 5.20.

EXAMPLE 2

A mixture of 1.32 g of 60% sodium hydride and 100 ml of dry toluene was incorporated dropwise with a solution of 3.39 g of azacycloheptane-2-one in toluene, heated under reflux for one hour, thereafter incorporated with 22.0 g of 1,6-dibromohexane and then further refluxed for 12 hours to obtain a reaction mixture. The thus obtained reaction mixture was washed with water, dried, freed from the solvent by distillation off at reduced pressure and then finally distilled to obtain a light-yellow substance. The thus obtained substance was added to a mixture of 6.24 g of n-pentylmercaptane, 5.47 g of 1,8-diazabicyclo [5,4,0] undecene-7 (DBU) and 100 ml of benzene, after which the whole was heated under agitation at 40°–60° C. for 5 hours, extracted with ethyl acetate, washed with water, dried, freed from the solvent by distillation off at reduced pressure and then finally distilled to obtain 6.69 g of colorless 1-[6-(n-pentylthio) hexyl] azacycloheptane-2-one having the following appearance, column temperature and analysis:

Appearance: Colorless transparent oil.
Column temp.: 146°–150° C./0.5 mmHg.
Analysis: $C_{17}H_{33}NOS$ Theoretical: C 68.17, H 11.10, N 4.68. Found: C 68.20, H 11.29, N 4.75.

EXAMPLE 3

1.29 g of 1-(2-hydroxyethyl)-2-pyrrolidone, 4.14 g of n-nonylbromide, 2.24 g of potassium hydroxide in a powder state and 30 ml of dimethyl sulfoxide were mixed together and agitated at room temperature for a whole day. The resulting reaction mixture was extracted with dichloromethane, after which the thus obtained extract was washed with water, dried, feed from the solvent by distillation off and then finally distilled to obtain 2.37 g of colorless 1-[2-(n-nonyloxy) ethyl] azacyclopentane-2-one having the following appearance, column temperature and analysis:

Appearance: Colorless transparent oil.
Column temp.: 109°–115° C./0.2 mmHg.
Analysis: $C_{15}H_{29}NO_2$ Theoretical: C 70.54, H 11.44, N 5.48. Found: C 70.37, H 11.58, N 5.39.

EXAMPLE 4

A mixture of 0.93 g of 60% sodium hydride and 100 ml of dry toluene was incorporated dropwise with 3.00 g of n-octyl alcohol, heated under reflux for one hour, thereafter incorporated with 14.1 g of 1,3-dibromopropane, further refluxed for 12 hours and then filtered to remove insoluble materials to obtain a filtrate. The thus obtained filtrate was washed with water, dried, freed from the solvent by distillation off and then finally distilled to obtain a colorless transparent substance. 4.59 g of the thus obtained substance was added to a mixture of 2.07 g of azacycloheptane-2-one, 0.80 g of 60% sodium hydride and 150 ml of dry toluene, after which the whole was refluxed for 12 hours and then filtered to remove insoluble materials to obtain a filtrate. The thus obtained filtrate was washed with water, dried, freed from the solvent by distillation off at reduced pressure and then finally distilled to obtain 3.60 g of colorless 1-[3-(n-octyloxy) propyl] azacycloheptane-2-one having the following appearance, column temperature and analysis:

Appearance: Colorless transparent oil.
Column temp.: 121°–124° C./0.3 mmHg. 048823595
Analysis: $C_{17}H_{33}NO_2$ Theoretical: C 72.04, H 11.73, N 4.94. Found: C 71.92, H 11.85, N 4.91.

EXAMPLE 5

A mixture of 0.88 g of 60% sodium hydride and 200 ml of dry toluene was incorporated dropwise with a solution of 2.26 g of azacycloheptane-2-one in toluene, heated under reflux for one hour, thereafter incorporated with 17.3 g of 1,4-dibromobutane, further refluxed for 18 hours and then filtered to remove insoluble materials to obtain a filtrate. The thus obtained filtrate was washed with water, dried, freed from the solvent by distillation off at reduced pressure and then finally distilled to obtain an oily substance. A mixture of 3.92 g of the thus obtained oily substance, 1.82 g of n-heptylamine and 50 ml of benzene was incorporated dropwise with 2.64 g of 1,8-diazabicyclo [5,4,0] undecene-7 (DBU) in benzene and agitated at room temperature for a whole day. The thus obtained reaction mixture (liquid state) was washed with water, dried, freed from the solvent by distillation off at reduced pressure and then finally distilled to obtain 3.16 g of colorless 1-[4-(n-heptylamino) butyl] azacycloheptane-2-one having the following appearance, column temperature and analysis:

Appearance: Colorless transparent oil.
Column temp.: 129°–133° C./0.2 mmHg.
Analysis: $C_{17}H_{34}N_2O$ Theoretical: C 72.29, H 12.13, N 9.92. Found: C 72.18, H 12.10, N 9.85.

EXAMPLE 6

3.04 g of methyl salicylate and 18.4 g of 1,5-dibromopentane were added to a solution of 1.06 g of 50% sodium hydride in toluene, heated to 100° C. for 3 hurs, washed with water, dried, freed from the solvent by distillation off at reduced pressure and then further distilled to obtain an oily substance. A mixture of the thus obtained oily substance and 2.70 g of sodium salt of azacycloheptane-2-one was heated to 100° C. in toluene solvent for 5 hours, washed with water, dried and freed from the solvent by distillation off at reduced pressure and then finally distilled to obtain 4.90 g of colorless 1-[5-(2-methoxycarbonylphenoxy) pentyl] azacycloheptane-2-one having the following appearance, column temperature and analysis:

Appearance: Colorless transparent oil.
Column temp.: 192°–198° C./0.2 mmHg.
Analysis: $C_{19}H_{27}NO_4$ Theoretical: C 68.44, H 8.16, N 4.20. Found: C 68.30, H 8.19, N 4.21.

EXAMPLE 7

5.24 g of 1-(5-bromopentyl) azacycloheptane-2-one, 1.34 g of 2-(n-butylthio) ethanol, 2.24 g of powderly potassium hydroxide and 30 ml of dimethylsulfoxide were mixed together, agitated at room temperature for 10 hours, extracted with dichloromethane to obtain an extract. The thus obtained extract was washed with water, dried, freed from the solvent by distillation off at reduced pressure and then finally distilled to obtain 2.84 g of colorless 1-[5-(2-butylthioethyl) oxypentyl] azacycloheptane-2-one having the following appearance, column temperature and analysis:

Appearance: Colorless transparent oil.
Column temp.: 151°–156° C./0.2 mmHg.
Analysis: $C_{17}H_{33}NO_2S$ Theoretical: C 64.72, H 10.54, N 4.44. Found: C 64.79, H 10.43, N 4.56.

EXAMPLE 8

1.98 g of L-2-pyrrolidone-5-carboxylic acid and 50 ml of ethanol were mixed together, agitated under cooling with iced water while blowing hydrogen chloride gas into the reaction system for one hour, and then freed from the solvent by distillation off at reduced pressure. The reaction mixture was incorporated with ethanol and then further distilled at reduced pressure to remove the ethanol. After this procedure was repeated twice, the residue obtained was incorporated with water and then an aqueous solution of sodium hydrogen carbonate so that the whole mass has a pH value of 9.0, extracted with chloroform, washed with water, dried and then freed from the solvent by distillation off at reduced pressure to obtain an oily substance. A solution of 3.05 g of the thus obtained oily substance in toluene was added to a mixture of 0.85 g of 60% sodium hydride and 100 ml of dry toluene, heated under reflux for one hour, thereafter incorporated with 2.35 g of allylbromide and then further refluxed for 3 hours to obtain a reaction mixture. The thus obtained reaction mixture was washed with water, dried and freed from the solvent by distillation off at reduced pressure to obtain an oily substance. 3.16 g of the thus obtained oily substance, 2.79 g of n-decylmercaptane, 13.2 mg of azobisisobutyronitrile and 40 ml of benzene were mixed together, and agitated under heat at the refluxing temperature for 6 hours to obtain a reaction mixture which was washed with water, dried and freed from the solvent by distillation off at reduced pressure to obtain a residue. The thus obtained residue was subjected to column chromatography and finally distilled to obtain 2.87 g of 1-[3-(n-decylthio) propyl]-5-ethoxycarbonyl-1-azacyclopentane-2-one having the following appearance, column temperature and analysis:

Appearance: Colorless transparent oil.
Column temp.: 172°–177° C./0.2 mmHg.
Analysis: $C_{20}H_{37}NO_3S$ Theoretical: C 64.65, H 10.04, N 3.77. Found: C 64.78, H 9.82, N 3.85.

EXAMPLE 9

A mixture of 3.00 g of 60% sodium hydride and 100 ml of benzene was incorporated dropwise with a solution of 3.00 g of L-2-amino-1-propanol in 10 ml of benzene, thereafter agitated at room temperature for a whole day, freed from the solvent by distillation off at reduced pressure to obtain a residue which was dissolved in ethyl acetate and subjected to column chromatography thereby to obtain 3.25 g of 5-methyl-3-morpholinone. A mixture of 1.24 g of 60% sodium hydride and 100 ml of toluene was incorporated dropwise with a solution of 3.25 g of 5-methyl-3-morpholinone in 10 ml of toluene, refluxed for one hour, incorporated with 7.05 g of lauryl bromide, further refluxed for a whole day, filtered to remove insoluble materials. The filtrate obtained was washed, dried and freed from the solvent by distillaton off at reduced pressure, subjected to column chromatography and finally distilled to obtain 5.69 g of colorless 4-(n-dodecyl)-5-methyl-3-morpholinone having the following appearance, column temperature and analysis:

Appearance: Colorless transparent oil.
Column temp.: 124°–130° C./0.2 mmHg.
Analysis: $C_{17}H_{33}NO_2$ Theoretical: C 72.04, H 11.73, N 4.94. Found: C 72.16, H 11.65, N 4.98.

EXAMPLES 10–133

The compounds represented by the formula (I) were prepared in the same manner as in Examples 1–9. The symbols used in formula of the compounds and the column temperature are shown in Table 1.

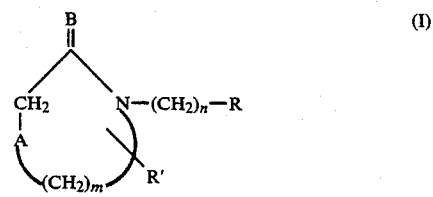

(I)

TABLE 1

| Example No. | A | B | m | n | R | R' | Column Temp. (°C./mmHg) |
|---|---|---|---|---|---|---|---|
| 10. | $CH_2$ | O | 1 | 2 | $-S-(CH_2)_5-CH_3$ | H | 111–117/0.5 |
| 11 | $CH_2$ | O | 1 | 2 | $-S-(CH_2)_7-CH_3$ | H | 117–122/0.2 |
| 12 | $CH_2$ | O | 1 | 2 | $-S-(CH_2)_9-CH_3$ | H | 130–135/0.2 |
| 13 | $CH_2$ | O | 1 | 2 | $-S-(CH_2)_{10}-CH_3$ | H | 142–148/0.4 |

TABLE 1-continued

| Example No. | A | B | m | n | R | R' | Column Temp. (°C./mmHg) |
|---|---|---|---|---|---|---|---|
| 14 | $CH_2$ | O | 1 | 3 | $-S-(CH_2)_7-CH_3$ | H | 122-128/0.2 |
| 15 | $CH_2$ | O | 1 | 3 | $-S-(CH_2)_8-CH_3$ | H | 128-132/0.2 |
| 16 | $CH_2$ | O | 1 | 3 | $-S-(CH_2)_9-CH_3$ | H | 134-139/0.2 |
| 17 | $CH_2$ | O | 1 | 4 | $-S-(CH_2)_6-CH_3$ | H | 125-131/0.2 |
| 18 | $CH_2$ | O | 1 | 4 | $-S-(CH_2)_7-CH_3$ | H | 130-134/0.2 |
| 19 | $CH_2$ | O | 1 | 5 | $-S-(CH_2)_5-CH_3$ | H | 124-129/0.2 |
| 20 | $CH_2$ | O | 1 | 5 | $-S-(CH_2)_6-CH_3$ | H | 129-134/0.2 |
| 21 | $CH_2$ | O | 1 | 5 | $-S-(CH_2)_9-CH_3$ | H | 155-160/0.5 |
| 22 | $CH_2$ | O | 1 | 6 | $-S-(CH_2)_4-CH_3$ | H | 126-131/0.2 |
| 23 | $CH_2$ | O | 1 | 6 | $-S-(CH_2)_5-CH_3$ | H | 129-133/0.2 |
| 24 | $CH_2$ | O | 1 | 6 | $-S-CH_2CH(CH_2CH_3)(CH_2CH_2CH_2CH_3)$ | H | 144-149/0.2 |
| 25 | $CH_2$ | O | 1 | 7 | $-S-(CH_2)_9-CH_3$ | H | 175-181/0.5 |
| 26 | $CH_2$ | O | 1 | 8 | $-S-(CH_2)_2-CH_3$ | H | 144-150/0.8 |
| 27 | $CH_2$ | O | 2 | 3 | $-S-(CH_2)_8-CH_3$ | H | 138-143/0.2 |
| 28 | $CH_2$ | O | 2 | 3 | $-S-(CH_2)_9-CH_3$ | H | 143-149/0.2 |
| 29 | $CH_2$ | O | 3 | 3 | $-S-(CH_2)_6-CH_3$ | H | 130-134/0.2 |
| 30 | $CH_2$ | O | 3 | 3 | $-S-(CH_2)_7-CH_3$ | H | 140-144/0.3 |
| 31 | $CH_2$ | O | 3 | 3 | $-S-(CH_2)_8-CH_3$ | H | 142-147/0.2 |
| 32 | $CH_2$ | O | 3 | 3 | $-S-(CH_2)_9-CH_3$ | H | 145-151/0.2 |
| 33 | $CH_2$ | O | 3 | 4 | $-S-(CH_2)_2-CH_3$ | H | 122-126/0.3 |
| 34 | $CH_2$ | O | 3 | 4 | $-S-(CH_2)_3-CH_3$ | H | 127-131/0.5 |
| 35 | $CH_2$ | O | 3 | 4 | $-S-(CH_2)_4-CH_3$ | H | 137-141/0.3 |
| 36 | $CH_2$ | O | 3 | 4 | $-S-(CH_2)_5-CH_3$ | H | 134-139/0.2 |
| 37 | $CH_2$ | O | 3 | 4 | $-S-(CH_2)_6-CH_3$ | H | 145-150/0.3 |
| 38 | $CH_2$ | O | 3 | 4 | $-S-(CH_2)_7-CH_3$ | H | 154-159/0.3 |
| 39 | $CH_2$ | O | 3 | 4 | $-S-(CH_2)_8-CH_3$ | H | 148-152/0.2 |
| 40 | $CH_2$ | O | 3 | 5 | $-S-(CH_2)_3-CH_3$ | H | 133-138/0.3 |
| 41 | $CH_2$ | O | 3 | 5 | $-S-(CH_2)_4-CH_3$ | H | 141-146/0.5 |
| 42 | $CH_2$ | O | 3 | 5 | $-S-(CH_2)_5-CH_3$ | H | 145-149/0.5 |
| 43 | $CH_2$ | O | 3 | 5 | $-S-(CH_2)_6-CH_3$ | H | 144-149/0.2 |
| 44 | $CH_2$ | O | 3 | 5 | $-S-(CH_2)_{11}-CH_3$ | H | 172-177/0.2 |
| 45 | $CH_2$ | O | 3 | 5 | $-S-(CH_2)_3-CH(CH_3)CH_3$ | H | 136-142/0.2 |
| 46 | $CH_2$ | O | 3 | 6 | $-S-(CH_2)_2-CH_3$ | H | 134-138/0.5 |
| 47 | $CH_2$ | O | 3 | 6 | $-S-(CH_2)_3-CH_3$ | H | 140-144/0.5 |
| 48 | $CH_2$ | O | 3 | 6 | $-S-(CH_2)_5-CH_3$ | H | 143-148/0.2 |
| 49 | $CH_2$ | O | 3 | 7 | $-S-(CH_2)_3-CH_3$ | H | 139-144/0.2 |
| 50 | $CH_2$ | O | 3 | 8 | $-S-(CH_2)_2-CH_3$ | H | 146-150/0.5 |
| 51 | $CH_2$ | O | 3 | 8 | $-S-(CH_2)_3-CH_3$ | H | 154-159/0.5 |
| 52 | $CH_2$ | O | 3 | 9 | $-S-CH_2CH_3$ | H | 158-164/0.5 |
| 53 | $CH_2$ | O | 3 | 9 | $-S-(CH_2)_7-CH_3$ | H | 177-183/0.3 |
| 54 | $CH_2$ | O | 3 | 10 | $-S-(CH_2)_2-CH_3$ | H | 165-171/0.6 |
| 55 | $CH_2$ | O | 3 | 10 | $-S-(CH_2)_3-CH_3$ | H | 162-167/0.5 |
| 56 | $CH_2$ | O | 1 | 2 | $-O-(CH_2)_7-CH_3$ | H | 99-105/0.2 |
| 57 | $CH_2$ | O | 1 | 2 | $-O-(CH_2)_9-CH_3$ | H | 115-121/0.2 |
| 58 | $CH_2$ | O | 1 | 2 | $-O-(CH_2)_{10}-CH_3$ | H | 127-133/0.3 |
| 59 | $CH_2$ | O | 1 | 3 | $-O-(CH_2)_7-CH_3$ | H | 105-111/0.2 |
| 60 | $CH_2$ | O | 1 | 3 | $-O-(CH_2)_8-CH_3$ | H | 111-117/0.2 |
| 61 | $CH_2$ | O | 1 | 3 | $-O-(CH_2)_9-CH_3$ | H | 122-127/0.2 |
| 62 | $CH_2$ | O | 1 | 4 | $-O-(CH_2)_6-CH_3$ | H | 108-112/0.2 |
| 63 | $CH_2$ | O | 1 | 4 | $-O-(CH_2)_7-CH_3$ | H | 118-122/0.2 |
| 64 | $CH_2$ | O | 1 | 4 | $-O-CH_2CH(CH_3)-(CH_2)_3-CH_3$ | H | 105-110/0.2 |
| 65 | $CH_2$ | O | 1 | 5 | $-O-(CH_2)_5-CH_3$ | H | 110-115/0.2 |
| 66 | $CH_2$ | O | 1 | 5 | $-O-(CH_2)_6-CH_3$ | H | 117-121/0.2 |
| 67 | $CH_2$ | O | 1 | 6 | $-O-(CH_2)_4-CH_3$ | H | 111-115/0.2 |
| 68 | $CH_2$ | O | 1 | 6 | $-O-(CH_2)_5-CH_3$ | H | 118-122/0.2 |
| 69 | $CH_2$ | O | 2 | 2 | $-O-(CH_2)_{11}-CH_3$ | H | 160-165/0.5 |
| 70 | $CH_2$ | O | 2 | 4 | $-O-(CH_2)_7-CH_3$ | H | 124-129/0.2 |
| 71 | $CH_2$ | O | 3 | 3 | $-O-(CH_2)_8-CH_3$ | H | 125-129/0.2 |
| 72 | $CH_2$ | O | 3 | 3 | $-O-(CH_2)_9-CH_3$ | H | 131-136/0.2 |
| 73 | $CH_2$ | O | 3 | 4 | $-O-(CH_2)_6-CH_3$ | H | 117-122/0.2 |
| 74 | $CH_2$ | O | 3 | 4 | $-O-(CH_2)_7-CH_3$ | H | 129-132/0.2 |
| 75 | $CH_2$ | O | 3 | 5 | $-O-(CH_2)_3-CH_3$ | H | 108-113/0.2 |
| 76 | $CH_2$ | O | 3 | 5 | $-O-(CH_2)_5-CH_3$ | H | 119-122/0.2 |
| 77 | $CH_2$ | O | 3 | 5 | $-O-(CH_2)_6-CH_3$ | H | 127-132/0.2 |
| 78 | $CH_2$ | O | 3 | 6 | $-O-(CH_2)_3-CH_3$ | H | 118-122/0.4 |

TABLE 1-continued

| Example No. | A | B | m | n | R | R' | Column Temp. (°C./mmHg) |
|---|---|---|---|---|---|---|---|
| 79 | CH$_2$ | O | 3 | 6 | —O—(CH$_2$)$_4$—CH$_3$ | H | 121–125/0.2 |
| 80 | CH$_2$ | O | 3 | 6 | —O—(CH$_2$)$_5$—CH$_3$ | H | 129–132/0.2 |
| 81 | CH$_2$ | O | 3 | 7 | —O—(CH$_2$)$_9$—CH$_3$ | H | 152–156/0.2 |
| 82 | CH$_2$ | O | 1 | 4 | —NH—(CH$_2$)$_7$—CH$_3$ | H | 130–135/0.2 |
| 83 | CH$_2$ | O | 1 | 4 | —N(CH$_2$CH$_3$)((CH$_2$)$_2$—CH$_3$) | H | 111–116/0.2 |
| 84 | CH$_2$ | O | 1 | 6 | —NHCH$_2$CH(CH$_3$)CH$_3$ | H | 117–121/0.2 |
| 85 | CH$_2$ | O | 1 | 6 | —N(CH$_2$CH$_3$)$_2$ | H | 108–113/0.2 |
| 86 | CH$_2$ | O | 3 | 4 | —NH—(CH$_2$)$_5$—CH$_3$ | H | 127–131/0.2 |
| 87 | CH$_2$ | O | 3 | 4 | —NH—(CH$_2$)$_7$—CH$_3$ | H | 135–139/0.2 |
| 88 | CH$_2$ | O | 3 | 5 | —NH—(CH$_2$)$_5$—CH$_3$ | H | 128–132/0.2 |
| 89 | CH$_2$ | O | 3 | 5 | —NH—(CH$_2$)$_6$—CH$_3$ | H | 129–134/0.2 |
| 90 | CH$_2$ | O | 3 | 6 | —NH—(CH$_2$)$_4$—CH$_3$ | H | 127–131/0.2 |
| 91 | CH$_2$ | O | 3 | 6 | —N((CH$_2$)$_2$—CH$_3$)$_2$ | H | 120–125/0.2 |
| 92 | CH$_2$ | O | 3 | 6 | —N(CH$_3$)((CH$_2$)$_5$—CH$_3$) | H | 134–139/0.2 |
| 93 | CH$_2$ | O | 1 | 6 | —O—C$_6$H$_4$—COOC$_2$H$_5$ (ortho) | H | 181–186/0.2 |
| 94 | CH$_2$ | O | 1 | 6 | —OCO—C$_6$H$_4$—OH (ortho) | H | 173–178/1.0 |
| 95 | CH$_2$ | O | 1 | 6 | —OCO—C$_6$H$_4$—OCH$_3$ (ortho) | H | 183–187/0.2 |
| 96 | CH$_2$ | O | 3 | 3 | —OCO—C$_6$H$_4$—OH (ortho) | H | 178–182/0.2 |
| 97 | CH$_2$ | O | 3 | 3 | —OCO—C$_6$H$_4$—OCH$_3$ (ortho) | H | 177–182/0.2 |

TABLE 1-continued
| Example No. | A | B | m | n | R | R' | Column Temp. (°C./mmHg) |
|---|---|---|---|---|---|---|---|
| 98 | $CH_2$ | O | 3 | 4 | 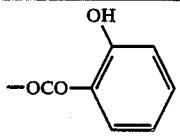 | H | 175–181/0.2 |
| 99 | $CH_2$ | O | 3 | 4 | 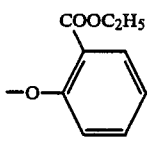 | H | 183–187/0.2 |
| 100 | $CH_2$ | O | 3 | 4 | 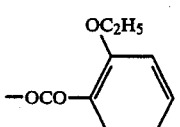 | H | 164–168/0.3 |
| 101 | $CH_2$ | O | 3 | 4 | 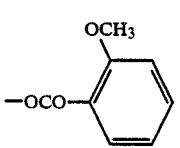 | H | 193–197/0.1 |
| 102 | $CH_2$ | O | 3 | 4 | 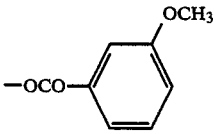 | H | 168–173/0.3 |
| 103 | $CH_2$ | O | 3 | 4 | 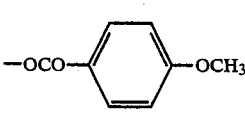 | H | 175–180/0.3 |
| 104 | $CH_2$ | O | 3 | 4 | 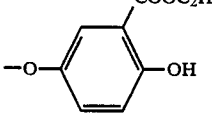 | H | 188–194/0.1 |
| 105 | $Ch_2$ | O | 3 | 4 | 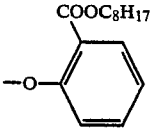 | H | 205–210/0.2 |
| 106 | $CH_2$ | O | 3 | 5 | 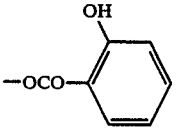 | H | 182–188/0.2 |
| 107 | $CH_2$ | O | 3 | 5 | 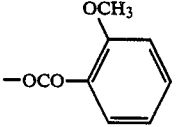 | H | 187–191/0.2 |
| 108 | $CH_2$ | O | 3 | 6 | 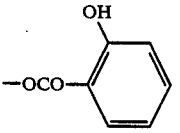 | H | 197–203/0.1 |

TABLE 1-continued

| Example No. | A | B | m | n | R | R' | Column Temp. (°C./mmHg) |
|---|---|---|---|---|---|---|---|
| 109 | CH₂ | O | 3 | 6 | -OCO-C₆H₄-OCH₃ (o) | H | 218–222/0.1 |
| 110 | CH₂ | O | 3 | 6 | -O-C₆H₄-COOC₂H₅ (o) | H | 204–211/0.1 |
| 111 | CH₂ | O | 3 | 10 | -OCO-C₆H₄-OH (o) | H | 217–222/0.1 |
| 112 | CH₂ | O | 3 | 10 | -OCO-C₆H₄-OCH₃ (o) | H | 230–236/0.1 |
| 113 | CH₂ | O | 3 | 10 | -O-C₆H₄-COOC₂H₅ (o) | H | 223–228/0.1 |
| 114 | CH₂ | O | 3 | 4 | -O-C₆H₄-COOH (o) | H | m.p. 83–93° C. |
| 115 | CH₂ | O | 1 | 6 | —S—(CH₂)₂—S—(CH₂)₂—CH₃ | H | 155–160/0.2 |
| 116 | CH₂ | O | 3 | 5 | —S—(CH₂)₂—S—(CH₂)₃—CH₃ | H | 167–173/0.2 |
| 117 | CH₂ | O | 3 | 5 | —O—(CH₂)₂—O—(CH₂)₃—CH₃ | H | 116–121/0.2 |
| 118 | CH₂ | O | 1 | 4 | —S—(CH₂)₆—CH₃ | 5-CH₃ | 127–133/0.2 |
| 119 | CH₂ | O | 1 | 4 | —O—(CH₂)₆—CH₃ | 5-COOC₂H₅ | 146–151/0.2 |
| 120 | CH₂ | O | 3 | 5 | —O—(CH₂)₅—CH₃ | 7-CH₃ | 122–126/0.2 |
| 121 | S | O | 1 | 3 | —S—(CH₂)₉—CH₃ | 5-COOC₂H₅ | 187–193/0.2 |
| 122 | O | O | 1 | 4 | —NH—(CH₂)₇—CH₃ | H | 125–130/0.2 |
| 123 | S | O | 1 | 11 | —CH₃ | H | 136–142/0.2 |
| 124 | S | O | 1 | 11 | —CH₃ | 5-(CH₂)₁₀—CH₃ | 236–244/0.2 |
| 125 | S | O | 2 | 3 | —O—(CH₂)₉—CH₃ | 5-CH₃ | 147–153/0.2 |
| 126 | O | O | 2 | 3 | —S—(CH₂)₉—CH₃ | 5-CH₃ | 150–155/0.2 |
| 127 | S | O | 2 | 11 | —CH₃ | H | 142–148/0.2 |
| 128 | S | O | 3 | 4 | —O—(CH₂)₆—CH₃ | H | 135–141/0.2 |
| 129 | O | O | 3 | 5 | —NH—(CH₂)₅—CH₃ | H | 123–128/0.2 |
| 130 | S | O | 3 | 11 | —CH₃ | H | 148–154/0.2 |
| 131 | CH₂ | S | 1 | 2 | —S—(CH₂)₉—CH₃ | H | 165–170/0.2 |
| 132 | CH₂ | S | 1 | 2 | —O—(CH₂)₉—CH₃ | H | 139–144/0.2 |
| 133 | CH₂ | S | 3 | 4 | —S—(CH₂)₆—CH₃ | H | 167–172/0.2 |

EXAMPLE 134

There was prepared a test ointment having the following formulation:

| | wt. % |
|---|---|
| Ketoprofen | 5.0 |
| Propylene glycol | 3.0 |
| Isopropyl myristate | 2.0 |
| White vaseline | 87.0 |
| Compound of this invention (Ex. 37) | 3.0 |

EXAMPLE 135

There was prepared a test solution (liniment) having the following formulation:

|  | wt. % |
|---|---|
| Ketoprofen | 2.8 |
| Ethanol | 47.1 |
| Purified water | 47.1 |
| Compound of this invention (Ex. 12) | 3.0 |

There were investigated the effects of the compound of this invention on the percutaneous penetration of ketoprofen using the dorsal skin of female hairless mice (each 9 weeks old) by a diffusion cell method which comprised adding 0.5 ml of said test solution to the donor side and measuring the amount of ketoprofen permeated into the receptor layer by performance liquid chromatography (HPLC). For comparison, the above procedure was followed except that a control solution containing no compound of this invention was substituted for said test solution containing the compound of this invention. The results are as shown in Table 2.

TABLE 2

| Test compound | Mice used in test | Cumulative amount of Ketoprofen permeated (μM) | | Activity |
|---|---|---|---|---|
| | | 24 hrs later | 48 hrs later | |
| Control (Vehicle: Non-use of compound of this invention) | 2 | 15.5 ± 2.0 | 42.4 ± 5.9 | 1.0 |
| Compound of Example 12 | 4 | 64.6 ± 9.3 | 140.4 ± 0.4 | 3.3 |

Note:
$$\text{Activity} = \frac{\text{Amount of ketoprofen permeated for 48 hours in test group}}{\text{Amount of ketoprofen permeated for 48 hours in control group}}$$

As is seen from Table 2, the compound of this invention added exhibited a remarkable promoting effect on the penetration of ketoprofen.

EXAMPLE 136

There was prepared a test solution for aerosol having the following formulation:

|  | wt. % |
|---|---|
| Ketoprofen | 1.0 |
| Isopropyl myristate | 1.0 |
| Ethanol | 20.0 |
| Fleon | 75.0 |
| Compound of this invention (Ex. 12) | 3.0 |

EXAMPLE 137

There was prepared a test hydrophylic ointment having the following formulation:

|  | wt. % |
|---|---|
| Indomethacin | 1.0 |
| White vaseline | 25.0 |
| Stearyl alcohol | 20.0 |
| Propylene glycol | 12.0 |
| HCO-60 | 4.0 |
| Methyl p-oxybenzoic acid | 0.1 |
| Propyl p-oxybenzoic acid | 0.1 |
| Purified water | 34.8 |
| Compound of this invention (Ex. 12) | 3.0 |

The activity of the compound of this invention was evaluated by means of a diffusion cell method in the same manner as in Example 135 except that the above test ointment was substituted for the test solution.

The results are as shown in Table 3.

TABLE 3

| Test compound | Mice used in test | Cumulative amount of indomethacin permeated (μg/ml) | | Activity |
|---|---|---|---|---|
| | | 24 hrs later | 48 hrs later | |
| Control (Vehicle) | 5 | 0.7 ± 0.1 | 4.4 ± 0.4 | 1.0 |
| Compound of Example 12 | 5 | 5.1 ± 0.4 | 14.2 ± 0.7 | 3.2 |

Note:
$$\text{Activity} = \frac{\text{Amount of indomethacin permeated for 48 hours in test group}}{\text{Amount of indomethacin permeated for 48 hours in control group}}$$

As is seen from Table 3, the penetration of indomethacin was enhanced by the addition of the compound of the present invention.

EXAMPLE 138

There was prepared a test gel ointment having the following formulation:

|  | wt. % |
|---|---|
| Indomethacin | 1.0 |
| DIPA | 1.1 |
| Ethanol | 48.0 |
| Purified water | 46.9 |
| Compound of this invention (Ex. 12) | 3.0 |

The activity of the invention was evaluated by means of a diffusion cell method in the same manner as in Example 135 except that the above test ointment was substituted for the test solution.

The results are as shown in Table 4.

TABLE 4

| Test compound | Mice used in test | Cumulative amount of indomethacin permeated (μg/ml) | | Activity |
|---|---|---|---|---|
| | | 24 hrs later | 48 hrs later | |
| Control (Vehicle) | 5 | 0.24 ± 0.04 | 0.45 ± 0.06 | 1.0 |
| Compound of Example 12 | 5 | 1.90 ± 0.15 | 8.29 ± 0.71 | 18.4 |

Note:
$$\text{Activity} = \frac{\text{Amount of indomethacin permeated for 48 hours in test group}}{\text{Amount of indomethacin permeated for 48 hours in control group}}$$

As is seen from Table 4, the penetration of indomethacin was extremely enhanced by the addition of the compound of this invention.

EXAMPLE 139

There was prepared a test cream having the following formulation:

|  | wt. % |
|---|---|
| Prednisolone | 3.0 |
| Triethanolamine | 0.1 |
| Glycerin | 3.0 |
| Monostearyl glycerin | 4.0 |
| Stearic acid | 15.0 |
| Purified water | 69.9 |

-continued

| | wt. % |
|---|---|
| Compound of this invention (Ex. 71) | 5.0 |

EXAMPLE 140

There was prepared a test macrogol ointment having the following formulation:

| | wt. % |
|---|---|
| Disodium cromoglycate | 1.0 |
| Polyethylene glycol 4000 | 43.0 |
| Cetylalcohol | 5.0 |
| Polysorbate 60 | 5.0 |
| Isopropyl myristate | 5.0 |
| Propylene glycol | 15.0 |
| Polyethylene glycol 300 | 23.0 |
| Compound of this invention (Ex. 57) | 3.0 |

EXAMPLE 141

There was prepared a test solution having the following formulation:

| | wt. % |
|---|---|
| Pindolol | 4.0 |
| Propylene glycol | 46.5 |
| Ethanol | 46.5 |
| Compound of this invention shown in Table 5 | 3.0 |

There were provided groups each consisting of four Wistar-strain male rats each weighing 200 to 250 g and having their dorsal skin hair shorn with an electric shaver.

Each of the test solutions (pindolol-containing preparations) was applied to the shorn dorsal skin of test rats of one of the groups in an amount of 150 μl/2.5×2.5 cm² and then sealed up. Three hours after the application of the test solution, the blood of the test rats was collected and measured for serum concentration of pindolol by HPLC. The results are as shown in Table 5.

For comparison, the above procedure was followed except that there was used a control solution which was the same as said test solution except for non-use of any compounds of this invention, and also followed using a comparative test solution which was the same as the test solution except for the substitution of a comparative compound for the compound of this invention. The results are also shown in Table 5.

TABLE 5

| Test compound | Serum concentration of pindolol (ng/ml) | Activity |
|---|---|---|
| Control (Vehicle) | 16.8 ± 9.4 | 1.0 |
| Compound of Example 1 | 583.6 ± 102.7 | 30.0 |
| Compound of Example 16 | 538.4 ± 63.7 | 32.0 |
| Compound of Example 20 | 682.7 ± 88.2 | 40.6 |
| Azone | 400.2 ± 81.6 | 23.8 |
| Control (Vehicle) | 11.4 ± 2.7 | 1.0 |
| Compound of Example 12 | 545.1 ± 89.6 | 47.8 |
| 1-methyl-2-pyrrolidone | 21.8 ± 16.7 | 1.9 |
| 1-ethyl-2-pyrrolidone | 31.6 ± 27.5 | 2.8 |
| Pyrrolidone carbonic acid | 23.8 ± 12.9 | 2.1 |
| Control (Vehicle) | 23.6 ± 7.8 | 1.0 |
| Compound of Example 57 | 778.2 ± 78.4 | 33.0 |
| Compound of Example 66 | 713.2 ± 57.6 | 30.2 |
| Compound of Example 67 | 538.1 ± 70.7 | 22.8 |
| Azone | 465.7 ± 62.4 | 19.7 |

TABLE 5-continued

| Test compound | Serum concentration of pindolol (ng/ml) | Activity |
|---|---|---|
| Control (Vehicle) | 11.9 ± 4.2 | 1.0 |
| Compound of Example 2 | 151.7 ± 99.9 | 12.7 |
| Compound of Example 35 | 104.8 ± 29.5 | 8.8 |
| Compound of Example 37 | 193.1 ± 23.7 | 16.2 |
| Compound of Example 38 | 143.1 ± 104.8 | 12.0 |
| Compound of Example 50 | 78.3 ± 42.7 | 6.6 |
| DMSO | 12.0 ± 4.2 | 1.0 |
| Azone | 97.8 ± 62.7 | 8.2 |
| Control (Vehicle) | 12.3 ± 0.4 | 1.0 |
| Compound of Example 29 | 182.2 ± 99.8 | 14.8 |
| Compound of Example 30 | 156.0 ± 49.3 | 12.7 |
| Compound of Example 31 | 338.3 ± 52.5 | 27.5 |
| Compound of Example 36 | 241.3 ± 147.1 | 19.6 |
| Compound of Example 39 | 221.1 ± 16.6 | 18.0 |
| Compound of Example 43 | 199.1 ± 98.0 | 16.2 |
| Compound of Example 48 | 183.2 ± 66.0 | 14.9 |
| Compound of Example 49 | 285.3 ± 83.3 | 23.2 |
| Azone | 179.6 ± 42.3 | 14.6 |
| Control (Vehicle) | 12.5 ± 3.6 | 1.0 |
| Compound of Example 73 | 426.2 ± 73.8 | 34.1 |
| Compound of Example 74 | 360.7 ± 57.1 | 28.9 |
| Compound of Example 76 | 104.0 ± 54.6 | 8.3 |
| Azone | 160.2 ± 39.8 | 12.8 |
| Control (Vehicle) | 34.4 ± 22.2 | 1.0 |
| Compound of Example 4 | 1084.4 ± 134.2 | 31.5 |
| Compound of Example 72 | 937.1 ± 121.6 | 27.2 |
| Compound of Example 80 | 897.3 ± 129.3 | 26.1 |
| Azone | 821.2 ± 93.5 | 23.9 |

Note:
$$\text{Activity} = \frac{\text{Serum concentration of pindolol in test group}}{\text{Serum concentration of pindolol in control group}}$$

As is seen from Table 5, the use of the compound of this invention in the test solution exhibited a remarkable increase in percutaneous absorption of pindolol as compared with the control and also indicated a satisfactory promoting action on the absorption of pindolol as compared with the comparative compound. Further, the dorsal skin portions to which the test solution containing the compound of this invention was applied were not appreciated to form thereon anything unusual such as erythema or edema.

EXAMPLE 142

There was prepared a test solution having the following formulation:

| | wt. % |
|---|---|
| Pindolol | 0.4 |
| Ethanol | 48.3 |
| Water | 48.3 |
| Compound of this invention (Ex. 12) | 3.0 |

The activity of the present invention was evaluated by a diffusion cell method in the same manner as in Example 135 except that the above test solution was substituted for the test solution used in Example 135.

The results are as shown in Table 6.

TABLE 6

| Test compound | Mice used in test | Cumulative amount of pindolol permeated (μM) | | Activity |
|---|---|---|---|---|
| | | 24 hrs later | 48 hrs later | |
| Control (Vehicle) | 4 | 1.6 ± 0.1 | 3.7 ± 0.3 | 1.0 |
| Compound of Example 12 | 4 | 50.0 ± 7.0 | 127.6 ± 4.8 | 34.5 |
| 1-ethyl-2-pyrrolidone | 4 | 1.3 ± 0.1 | 2.7 ± 0.2 | 0.7 |

TABLE 6-continued

| Test compound | Mice used in test | Cumulative amount of pindolol permeated (μM) | | Activity |
|---|---|---|---|---|
| | | 24 hrs later | 48 hrs later | |
| Pyrolidone carbonic acid | 4 | 1.0 ± 0.0 | 1.9 ± 0.1 | 0.5 |

Note:

$$\text{Activity} = \frac{\text{Amount of pindolol permeated for 48 hours in test group}}{\text{Amount of pindolol permeated for 48 hours in control group}}$$

As is seen from Table 6, the compound of this invention added exhibited a remarkable promoting effect on the penetration of pindolol as compared with the control and also indicated a satisfactory activity as compared with the comparative compound.

EXAMPLE 143

There was prepared a test acryl tape having the following formulation:

| | weight (g) |
|---|---|
| Pindolol | 1.2 |
| Nicasol TS-444 ® | 37.68 |
| Citric acid | 0.6 |
| Compound of this invention (Ex. 12) | 0.72 |
| | 1.0 mg/cm² |

The activity of this invention was evaluated by means of a diffusion cell method in the same manner as in Example 135 except that the tape at the size of 0.785 cm² (including 0.8 mg of pindolol) was applied onto skin specimens. The results are as shown in Table 7.

TABLE 7

| Test compound | Cumulative amount of pindolol permeated (μg/ml) | | Activity |
|---|---|---|---|
| | 24 hrs later | 48 hrs later | |
| Control (Vehicle) | 339 ± 91 | 929 ± 25 | 1.0 |
| Compound of Example 12 | 1212 ± 30 | 3634 ± 54 | 3.9 |

Note:

$$\text{Activity} = \frac{\text{Amount of pindolol permeated for 48 hours in test group}}{\text{Amount of pindolol permeated for 48 hours in control group}}$$

As is seen from Table 7, the skin penetration of pindolol from the test tape was enhanced by addition of the compound of this invention.

EXAMPLE 144

There were prepared control and test solutions having the following respective formulations (Table 8):

TABLE 8

| | Control solution A | Control solution B | Test solution |
|---|---|---|---|
| Glibenclamide | 0 | 0.6 | 0.6 |
| Ethanol | 50 | 49.7 | 48.2 |
| Purified water | 50 | 49.7 | 48.2 |
| Compound of this invention (Ex. 12) | 0 | 0 | 3.0 |

(wt. %)

In the tests, there were used groups each consisting of four Wistar-strain male rats which weighed about 200 to 250 g and abstained from food for 24 hours.

Each of the control solutions A and B and the test solution indicated in the above Table 8 was applied to the dorsal skins, shorn by an electric clipper or shaver, of the rats of one group in an amount of 175 μl/2.5×2.5 cm² and then sealed up. Three hours after sealing up, 1.5 ml of 20% glucose was subcutaneously injected into said rats. Two hours after the glucose injection, the blood of the rats was collected and measured for glucose level in blood.

For comparison, the above procedure was followed except that azone was substituted for the compound of Example 12 in the test solution.

For further comparison, the blood of rats of one group which had been subjected only to 24 hours' abstinence from food (this group being hereinafter referred to as "normal group"), was measured for glucose level in blood. The rat groups to which the control solution A, the control solution B and the test solution were applied, are hereinafter referred to as "control group A", "control group B" and "test group", respectively. The test results are as shown in Table 9.

TABLE 9

| Group | Glucose level (mg/dl) | Inhibition rate (%) |
|---|---|---|
| Normal group | 70 ± 4 | — |
| Control group A | 154 ± 10 | — |
| Control group B | 157 ± 7 | −3.6 |
| Test group (use of compd. of Ex. 12) | 115 ± 4 | 46.4 |
| Azone group | 133 ± 13 | 25.0 |

Note:

$$\text{Inhibition rate} = \left\{ 1 - \frac{\text{(glucose level for control group B or test group − that for normal group)}}{\text{(glucose level for control group A − that for normal group)}} \right\} \times 100\ (\%)$$

As is seen from Table 9, the control group B (glibenclamide used alone) did not exhibit any effects on hypoglycemic activity as compared with the control group A, whereas the test group (compound of this invention used) exhibited a remarkable effect on the promotion of absorption of glibenclamide whereby the glibenclamide was percutaneously absorbed to lower the glucose level. In addition, the compound of this invention was appreciated to be more excellent in absorption-promoting action than Azone used as the comparative compound.

EXAMPLE 145

There was prepared a test emulsion having the following formulation:

| | wt. % |
|---|---|
| Glibenclamide | 1.0 |
| Monooleoilglycerin pilogulutamine ester | 47.0 |
| Purified water | 47.0 |
| Compound of this invention (Ex. 12) | 5.0 |

EXAMPLE 146

There was prepared a test solution having the following formulation:

|  | wt. % |
|---|---|
| 5-Fluorouracil (5-FU) | 1.8 |
| Ethanol | 47.6 |
| Water | 47.6 |
| Compound of this invention (Ex. 12) | 3.0 |

The activity of invention was evaluated by means of a diffusion cell method in the same manner as in Example 135 except that the above test solution was substituted for the test solution used in Example 135.

The results are as shown in Table 10.

TABLE 10

| Test compound | Mice used in test | Cumulative amount of 5-FU permeated ($\mu$M) | | Activity |
|---|---|---|---|---|
| | | 24 hrs later | 48 hrs later | |
| Control (Vehicle) | 3 | 104 ± 10 | 206 ± 26 | 1.0 |
| Compound of Example 12 | 4 | 465 ± 83 | 963 ± 22 | 4.7 |
| 1-methyl-2-pyrolidone | 4 | 83 ± 15 | 192 ± 20 | 0.9 |
| 1-ethyl-2-pyrolidone | 4 | 96 ± 15 | 178 ± 9 | 0.9 |

Note:
$$\text{Activity} = \frac{\text{Amount of 5-FU permeated for 48 hours in test group}}{\text{Amount of 5-FU permeated for 48 hours in control group}}$$

As is seen from Table 10, the addition of the compound of this invention significantly enhanced the penetration of 5-FU, as compared with the control and the comparative compounds didn't show any activity.

EXAMPLE 147

There was prepared a test solution having the following formulation:

|  | wt. % |
|---|---|
| Phenol red | 0.07 |
| Purified water | 96.93 |
| Compound of the invention shown in Table 11 | 3.0 |

There were investigated the effects of the compound of this invention on the percutneous penetration of phenol red which is difficult to be penetrated using the dorsal skin of female hairless mice (each 9 weeks old) by a diffusion cell method which comprised adding 0.5 ml of a sodium chloride injection containing 2 mM of phenol red to the donor side and measuring the amount of phenol red permeated into the receptor layer by high-pace optimal densitometric meter (559 nm).

The results are as shown in Table 11.

TABLE 11

| Test compound | Mice used in test | Cumulative amount of phenol red permeated ($\mu$M) | | Activity |
|---|---|---|---|---|
| | | 24 hrs later | 48 hrs later | |
| Control (Vehicle) | 8 | 0.0 ± 0.0 | 0.6 ± 0.2 | 1.0 |
| Compound of Example 12 | 3 | 24.5 ± 6.0 | 51.9 ± 9.9 | 86.5 |
| Compound of Example 37 | 3 | 15.0 ± 5.3 | 32.5 ± 1.3 | 54.2 |
| Compound of Example 57 | 3 | 18.3 ± 1.1 | 39.3 ± 0.6 | 65.5 |
| Compound of Example 73 | 3 | 17.8 ± 3.6 | 33.8 ± 5.8 | 56.3 |
| Azone | 3 | 8.4 ± 7.6 | 14.5 ± 0.7 | 24.2 |

Note:
$$\text{Activity} = \frac{\text{Amount of phenol red permeated for 48 hours in test group}}{\text{Amount of phenol red permeated for 48 hours in control group}}$$

As is seen from Table 11, the use of the compound of this invention in the test solution exhibited a remarkable promoting action on the absorption of phenol red as compared with the control and indicated a satisfactory promoting action as compared with the comparative compounds.

EXAMPLE 148

There was prepared a test lotion having the following formulation:

|  | wt. % |
|---|---|
| P—Aminobenzoic acid | 1.0 |
| Cetyl alcohol | 15.0 |
| Propylene glycol | 10.0 |
| Sodium laurate | 15.0 |
| Purified water | 50.0 |
| Compound of this invention (Ex. 101) | 9.0 |

EXAMPLE 149

There was prepared a test solution having the following formulation:

|  | wt. % |
|---|---|
| Drug shown in Table 12 | 1.0 |
| Ethanol | 48.0 |
| Purified water | 48.0 |
| Compound of this invention (Ex. 12) | 3.0 |

The activity of invention was evaluated by means of a diffusion cell method in the same manner as in Example 135 except that the above test solution was substituted for the test solution used in Example 135 and that the amounts of various drugs penetrated through the skin barrier were measured by using standard analytical techniques.

The results (mean value of 3–7 skin cells) are as shown in Table 12.

TABLE 12

| Drug | Test compound | Activity |
|---|---|---|
| Erythromycin | Compound of Example 12 | 4.5 |
| Clotrimazole | " | 3.2 |
| Triamcinolone | " | 5.5 |
| Chlordiazepoxide | " | 4.8 |
| Lidocain | " | 10.3 |
| Estradiol | " | 2.0 |
| Testosterone | " | 2.5 |
| Scopolamin | " | 2.4 |
| p-Aminobenzoic acid | " | 12.3 |
| Ketotifen | " | 3.8 |
| Clonidine | " | 6.3 |
| Nifedipine | " | 6.2 |
| Diazepam | " | 3.5 |
| Prostaglandin $E_2$ | " | 4.8 |
| 8-Bromocyclic AMP | " | 50.3 |
| 1,25-Dihydroxy $VD_3$ | " | 5.4 |

TABLE 12-continued

| Drug | Test compound | Activity |
|---|---|---|
| Nicotinic acid | " | 15.3 |

Note:

$$\text{Activity} = \frac{\text{Amount of test drug permeated for 48 hours in test group}}{\text{Amount of test drug permeated for 48 hours in control group}}$$

As is seen from Table 12, the use of the compound of this invention exhibited a remarkable increase in the penetration of various drugs.

EXAMPLE 150

There were prepared the following suppositories for use in normal, control and test groups, respectively, each group consisting of five male rabbits weighing 2.5 to 3.5 kg each.

TABLE 13

| | Suppository | | |
|---|---|---|---|
| | Normal group | Control group | Test group |
| Insulin (Bovine, International Unit) | — | 100 | 100 |
| Witepsol H-15 (%) | 100 | 100 | 97 |
| Compound of this invention (Ex. 12) (%) | — | — | 3 |

The three suppositories were into the rectums of the rabbit groups in an amount of 0.3 g suppository/kg, respectively. Thereafter, blood was collected from the rabbits through their ear vein three times with the lapse of time to measure the three collected blood samples for glucose level in blood by a glucose oxidase method. For comparison, the above procedure was followed except that Azone was substituted for the compound of Example 12. The results are indicated in terms of a change in glucose level in blood with respect to the glucose level in blood prior to the administration of the suppositories.

TABLE 14

| | Changes of glucose level to the initial (mg/dl) | | |
|---|---|---|---|
| Suppository | 0.5 hr | 1 hr | 3 hrs |
| Normal group | +4 | +7 | +0 |
| Control group | −1 | +3 | +1 |
| Test group (Compound of Example 12) | −30 | −29 | −22 |
| Azone group | −4 | +2 | +1 |

As is seen from Table 14, the control group (only insulin used) exhibited no effects on glucose level in blood as compared with the normal group. On the other hand, the test group (compound of this inventinn used) exhibited a remarkable hypoglycemic activity in blood and, in addition, did not exhibit any irritative symptoms at the mucous membrane of the rectum portion to which the suppository was inserted.

EXAMPLE 151

There was prepared the following suppositories of antibiotics for use in control and test groups, respectively, each group consisting of five male rabbits weighing 2.5 to 3.5 kg each.

TABLE 15

| ABPC suppository | | CET suppository | |
|---|---|---|---|
| Ampicillin Na | 6.0 | Cephalothin Na | 6.0 |
| Witepsol H-15 | 91.0 | Witepsol H-15 | 91.0 |
| Compound of this invention (Ex. 12) | 3.0 | Compound of this invention (Ex. 12) | 3.0 |

(wt. %)

Each of male rabbits was fasted for 24 hrs prior to the following Experiment. The two suppositories were into the rectums of the rabbit groups in an amount of 0.3 g suppository/kg, respectively. Thereafter, blood was collected from the rabbits through their ear vein to measure the collected blood samples for the serum concentration of antibiotic by HPLC. The results are as shown in Table 16.

TABLE 16

| | ABPC suppository | | | CET suppository | | |
|---|---|---|---|---|---|---|
| Test Compound | C max (μg/ml) | AUC (μg min/ml) | Activity | C max (μg/ml) | AUC (μg min/ml) | Activity |
| Control (Vehicle) | 1.4 ± 0.2 | 123.0 | 1.0 | 1.6 ± 0.3 | 150.0 | 1.0 |
| Compound of Example 12 | 20.0 ± 0.3 | 774.0 | 6.3 | 7.4 ± 0.4 | 443.0 | 3.0 |

Note:

$$\text{Activity} = \frac{\text{AUC of antibiotics in test group}}{\text{AUC of antibiotics in control group}}$$

As is seen from Table 16, the compound of the present invention demonstrated significantly enhancement on the rectal absorption of both antibiotics.

EXAMPLE 152

There was prepared test suppositories having the following formulations:

| | wt. % |
|---|---|
| Drug shown in Table 17 | 1.0 |
| Witepsol H-15 | 96.0 |
| Compound of this invention (Ex. 12) | 3.0 |

The same procedure of Example 151 was followed except that the above suppositories were used and that 3 or 4 rabbits were used in each group.

The results are as shown in Table 17.

TABLE 17

| Drug | Test compound | Activity |
|---|---|---|
| Indomethacin | Compound of Example 12 | 2.5 |
| 5-FU | Compound of Example 12 | 4.8 |

Note:

$$\text{Activity} = \frac{\text{AUC of each drug in test group}}{\text{AUC of each drug in control group}}$$

As is seen from Table 17, the compound of the present invention significantly enhanced the rectal absorption of indomethacin and 5-FU.

EXAMPLE 153

There was prepared a test suppository having the following formulation:

|  | wt. % |
| --- | --- |
| Ketoprofen | 3.0 |
| Cacao oil | 96.0 |
| Compound of this invention (Ex. 115) | 1.0 |

EXAMPLE 154

There was prepared a test tablet having the following formulation:

|  | wt. % |
| --- | --- |
| Chloramphenicol | 5.0 |
| Citric acid (nonhydrate) | 25.0 |
| Cellulose (crystal) | 35.0 |
| Corn starch | 20.0 |
| Hydroxypropyl cellulose | 10.0 |
| Magnesium stearate | 2.0 |
| Compound of this invention (Ex. 131) | 3.0 |

As shown in above results, when the compound of the present invention was added to the composition used as a drug, the absorption or penetration of active component through skin or mucosal membrane was extremely enhanced.

EXAMPLE 155

As one of tests on the compounds of this invention for their topical toxicity, a primary skin irritation test was made on skins using rabbits as the subjects. More particularly, an adhesive plaster for use in batch tests, to which 100 μl of a 3% test solution of each of the compounds of Examples 12, 37, 57 and 73 of this invention in 100 ml of polyethylene glycol 300 had dropwise been applied, was applied to the hair-shorn dorsal skin of three Japanese-native rabbits weighing 2.5 to 3.0 kg each and then sealed up on the dorsal skin for 24 hours. The rabbits were evaluated three times for their dorsal skin irritative reaction 24, 48 and 72 hours after removal of the plaster by using a method in accordance with the Draize's method.

For comparison, the above procedure was followed except that a control solution (polyethylene glycol only) was used instead of said 3% test solution, and it was further followed except that a comparative compound Azone was substituted for the compound of this invention in such a 3% test solution.

The results are as shown in Table 18 in which the overall evaluation is represented by the following equation.

$$\text{Overall evaluation} = \frac{\left(\begin{array}{c}\text{Evaluation at} \\ \text{24 hour later}\end{array} + \begin{array}{c}\text{Evaluation at} \\ \text{72 hours later}\end{array}\right)}{2}$$

and is graded into mild irritation (0–2 points), moderate irritation (2–6 points) and severe irritation (6–8 points).

TABLE 18

| Solution applied | Average irritation score | | | Overall evaluation |
| --- | --- | --- | --- | --- |
|  | 24 hours | 48 hours | 72 hours |  |
| Control solution | 0.4 ± 0.2 | 0.5 ± 0.3 | 0.0 ± 0.0 | Mild |
| Test solution (compd. of Ex. 12 contained) | 0.3 ± 0.3 | 0.3 ± 0.3 | 0.5 ± 0.5 | Mild |
| Test solution (compd. of Ex. 37 contained) | 0.6 ± 2 | 0.5 ± 0.5 | 0.5 ± 0.5 | Mild |
| Test solution (compd. of Ex. 57 contained) | 0.0 ± 0.0 | 0.3 ± 0.3 | 0.3 ± 0.3 | Mild |
| Test solution (compd. of Ex. 73 contained) | 0.3 ± 0.3 | 0.3 ± 0.3 | 0.5 ± 0.5 | Mild |
| Comparative solution (Azone contained) | 3.8 ± 1.3 | 3.8 ± 1.7 | 5.5 ± 1.9 | Moderate |

As is seen from Table 18, the compounds of this invention hardly exhibited any irritating actions on the skins as in the case of the control, and the comparative compound Azone, however, exhibited moderate grade irritating actions over a period of time of at least 72 hours.

It has been found from the above test that the compounds of this invention have extremely feeble irritating effects on skins.

EXAMPLE 156

As to whether the compounds of this invention have systemic toxicity, tests were made using rats to find whether the compounds would exert acute toxicity on the rats when they were orally or subcutaneously administered. More particularly, there were provided groups each consisting of 4–5 Wistar-strain male rats weighing 100–120 g each, and the compounds of this invention were administered to the groups so provided, respectively, one rat being administered in an amount of 0.5 ml/100 g. For one week after the administration, the rats of the groups were observed to know their general symptoms, change in weight and mortality. For comparison, the above procedure was repeated using comparative compound instead of the compounds of this invention. The results are as indicated in terms of $LD_{50}$ in the following Table 19.

TABLE 19

| Compound administered | Manner of administration $LD_{50}$ (g/kg) | |
| --- | --- | --- |
|  | Oral administration | Sabcutaneous administration |
| Compd. of Example 12 | >5 | >5 |
| Compd. of Example 37 | >5 | >5 |
| Compd. of Example 57 | >5 | >5 |
| Compd. of Example 73 | >5 | >5 |
| 1-methyl-2-pyrrolidone | 1 < x < 2 | 2 < x < 5 |
| 1-ethyl-2-pyrrolidone | 1 < x < 2 | 2 < x < 5 |
| Pyrrolidone carboxylic acid | 1 < x < 2 | 2 < x < 5 |
| Azone | >5 | >5 |

As is indicated in Table 19, the compounds of this invention did not cause unusual symptoms on the rats and death thereof after they had been orally or subcutaneously administered to the rats.

It is seen from the above results that the compounds of this invention have extremely high safety.

As is apparent from the results of the aforesaid Examples, as compared with the known compounds, the compounds of this invention have powerful actions on the permeation and absorption of medicines through live body membranes, particularly skins as well as the membranes of rectums, noses, mouths, vaginas or the like. The actions are effective for a wide variety of medicines or are enhancing pharmacological effects. Further, the compounds of this invention may be used together with a variety of bases and in various medicinal forms.

In addition, the compounds of this invention have been appreciated to have extremely feeble topical and systemic toxicities against live bodies and have therefore high safety.

[EFFECTS OR ADVANTAGES OF THIS INVENTION]

Azacycloalkane derivatives of this invention are compounds having a novel structure which were synthesized by the present inventors. They have powerful actions on the promotion of permeation and absorption of medicines through live body skins substantially without topical and systemic toxicities and consequently with high safety.

Further, a composition containing a compound of this invention together with a medicine are very useful both as a topical medicine which is expected to exert pharmacological actions at the skin, nose, mouth, rectum, vagina or the like where the composition is administered and as a systemic medicine which is expected to exert pharmacological actions throughout the whole body.

We claim:

1. An absorption promoting agent for application to live body membranes, comprising at least one member as the effective ingredient for promoting absorption, selected from azacycloalkane derivatives represented by the following general formula (I)

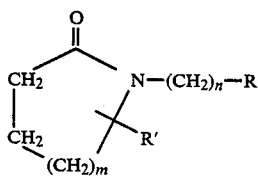

wherein R is —SR″ in which R″ is alkyl of 1–15 carbon atoms or —OR″ in which R″ alkyl of 1–15 carbon atoms, R′ is hydrogen, alkyl or an alkyloxycarbonyl having 1–12 carbon atoms, m is 1 or 3, and n is an integer of 2–8 or 3–10 with the proviso that m is 1 or 3 respectively.

2. An absorption promoting agent according to claim 1, wherein m is 1, n is an integer of 2–8, R is —SR″ in which R″ is an alkyl group having 5–11 or 3–11 carbon atoms with the proviso that n is an integer of 2–3 or 4–8 respectively, and R′ is a hydrogen atom.

3. An absorption promoting agent according to claim 1, wherein m is 3, n is an integer of 3–10, R is —SR″ in which R″ is an alkyl group having 5–12 or 2–12 carbon atoms with the proviso that n is 3 or an integer of 4–10 respectively, and R′ is a hydrogen atom.

4. An absorption promoting agent according to claim 1, wherein m is 1, n is an integer of 2–8, R is —OR″ in which R″ is an alkyl group having 5–11 carbon atoms, and R′ is a hydrogen atom.

5. An absorption promoting agent according to claim 1, wherein m is 3, n is an integer of 3–10, R is —OR″ in which R″ is an alkyl group having 4–10 carbon atoms, and R′ is a hydrogen atom.

6. An absorption promoting agent according to claim 1, wherein R is —SR″ in which R″ in an alkyl group or —OR″ in which R″ is as defined above, R′ is an alkyl group or alkyloxycarbonyl having 1–12 carbon atoms, m is 1 or 3, and n is an integer of 2–8 when m is 1 or an integer of 3–10 when m is 3.

7. The absorption promoting agent according to claim 1, wherein said effective ingredient is 1-[2-(n-decylthio) ethyl] azacyclopentane-2-one.

8. An external preparation for application to live body membranes, comprising a pharmaceutically-active agent and an absorption promoting agent comprising 0.001–25% of at least one member as the effective ingredient for promoting absorption, selected from azacycloalkane derivatives represented by the following general formula (I)

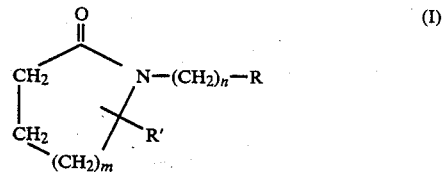

wherein R is —SR″ in which R″ is alkyl of 1–15 carbon atoms or —OR″ in which R″ is alkyl of 1–15 carbon atoms, R′ is hydrogen, alkyl or an alkyloxycarbonyl having 1–12 carbon atoms, m is 1 or 3 and n is an integer of 2–8 or 3–10 with the proviso that m is 1 or 3 respectively and inert excipients.

9. An external preparation according to claim 8 which is in the form of suppository, plaster, cataplasma, tape, paste, ointment, gel, cream, lotion, liniment or film.

10. An external preparation according to claim 8 wherein the pharmaceutically-active agent is an antibiotic, a chemotherapeutic agent, a bacteriostatic agent, an antimicrobial, a disinfectant, an antifungal agent, a non-steroidal anti-inflammatory agent, a steroidal anti-inflammatory agent, a carcinostatic agent, a psychotropic drug, a local anesthetic, an antiparkinsonian drug, a sex hormone drug, an anti-sudorific agent, a sunscreen, an antiallergic agent, an antiarrhythmic agent, an hypotensive agent, a vasodilator, a capillary stabilizer, a skeletal muscle relaxant, an antiemetic, an antipsoriatic drug, a skin softener, an emollient, a prostaglandin, a liposoluble vitamin, an enzyme, a peptide hormone, an antidiabetic drug, an insect repellent, an insecticide or an agricultural chemical.

* * * * *

UNITED STATES PATENT AND TRADEMARK OFFICE
CERTIFICATE OF CORRECTION

PATENT NO. : 4,882,359

DATED : November 21, 1989

INVENTOR(S) : Nakagawa, et al

It is certified that error appears in the above-identified patent and that said Letters Patent is hereby corrected as shown below:

On the title page item [75] should read as follow:

Akira Nakagawa, Tosu;

Michinori Sakai, Mizuma;

Mikio Nakashima, Tosu;

Masaru Saita, Miyaki;

Yuji Shimozono, Tosu;

Masayoshi Tsuji, Tosu;

Hisataka Inoue, Okawa;

Terumi Hachiya, Kanzaki, all of Japan

Signed and Sealed this

Seventh Day of May, 1991

*Attest:*

HARRY F. MANBECK, JR.

*Attesting Officer*      *Commissioner of Patents and Trademarks*